United States Patent [19]

Tomich et al.

[11] Patent Number: 5,268,284
[45] Date of Patent: Dec. 7, 1993

[54] RIBOSOME BINDING SITE

[75] Inventors: Che-Shen C. Tomich, Kalamazoo; Mary K. Olsen, Oshtemo, both of Mich.

[73] Assignee: The Upjohn Company, Kalamazoo, Mich.

[21] Appl. No.: 635,570

[22] PCT Filed: Feb. 23, 1989

[86] PCT No.: PCT/US89/00650
§ 371 Date: Aug. 27, 1990
§ 102(e) Date: Aug. 27, 1990

[87] PCT Pub. No.: WO89/08708
PCT Pub. Date: Sep. 21, 1989

Related U.S. Application Data

[63] Continuation-in-part of Ser. No. 166,882, Mar. 11, 1988, abandoned.

[51] Int. Cl.$^5$ .................... C07H 21/00; C12N 15/18; C12N 15/70; C12N 15/71
[52] U.S. Cl. .................... 435/172.3; 435/69.4; 435/320.1; 536/23.51; 536/24.1; 935/29; 935/39; 935/41
[58] Field of Search .................... 435/69.1, 69.4, 172.3, 435/172.1, 320.1; 935/41, 45, 13; 536/27, 23.51, 24.1, 24.2

[56] References Cited

U.S. PATENT DOCUMENTS 4,582,800  4/1986  Crowl ........................ 435/69.51

FOREIGN PATENT DOCUMENTS

46468/85  2/1986  Australia .
47600  3/1982  European Pat. Off. .
103395  3/1984  European Pat. Off. .
111814  6/1984  European Pat. Off. .
0173149  3/1986  European Pat. Off. .
0241446  10/1987  European Pat. Off. .
8806186  8/1988  PCT Int'l Appl. .
2073245A  10/1981  United Kingdom .

OTHER PUBLICATIONS

Cho, K. et al. "Sequence changes preceding a Shine--Dalgarno region influence trpE mRNA Translation and Decay," *J. Mol. Biol.* 204:51-60 (1988).

Seeburg, Peter H. "Efficient Bacterial Expression of Bovine and Porcine Growth Hormones", *DNA* 2:37-45, (1983).

George, Henry J. "High-level Expression in *E. coli* of Biologically Active Bovine Hormone," *DNA* 4:273-281 (1985).

Lewin, Benjamin *Genes III* pp. 193-200 (1987).

Schoner, B. E., et al., Role of mRNA Translational Efficiency in Bovine Growth Hormone Expression in *Escherichia coli*, PNAS USA, 81, pp. 5403-5407 (1984).

Gold, L., et al., Ann. Rev. Microbiol., 35, pp. 365-403 (1981).

Scherer, G. F. E., et al., Nucleic Acids Res., 17, pp. 3895-3906 (1980).

Marquis, D. M., J. M. Smolec and D. H. Katz, Gene, 42, pp. 175-183 (1986).

Vize, P. D. and Wells, J. R. E., FEBS Letters, 213, pp. 155-158 (1987).

DeBoer, Herman A., et al., DNA, 2, pp. 231-235 (1983).

*Primary Examiner*—Charles L. Patterson, Jr.
*Assistant Examiner*—Dian C. Jacobson
*Attorney, Agent, or Firm*—Sidney B. Williams, Jr.

[57] ABSTRACT

Provided are ribosome binding sites having an increased number of adenine (A) and thymidine (T) residues as compared to the naturally occurring ribosome binding sites from which they are derived or to which they are related, which allow high level expression of genes encoding heterologous polypeptides, particularly somatotropins, operatively linked thereto.

7 Claims, No Drawings

RIBOSOME BINDING SITE

This application is a continuation-in-part of Ser. No. 07/166,882, filed Mar. 11, 1981, now abandoned.

FIELD OF INVENTION

This invention relates to methods for enhancing expression of heterologous polypeptides. More specifically, the invention relates to the enhancement of expression of heterologous polypeptides by altering the ribosome binding sites operatively linked thereto.

BACKGROUND OF THE INVENTION

Some heterologous polypeptides, including bovine somatotropin (BSt), are difficult to express in most *E. coli* expression systems. Modifications within the first 4 codons of the CDNA encoding the BSt structural gene result in increased levels of BSt expression when these modified cDNAs are expressed in a pBR322-related vector. These modified cDNAs are expressed at even higher levels when placed in a runaway expression vector (U.S. patent application Ser. No. 016,294, filed 19 Feb. 1987 and incorporated herein by reference). The modified ribosome binding sites of the instant invention produce expression of heterologous polypeptides with a non-runaway vector, for example, a derivative of pIYR322, equivalent to that achieved with a runaway vector.

Generally, methods for cloning and expressing heterologous polypeptides in transformed hosts are well known to those skilled in the art. Such heterologous polypeptides include, for example, human insulin, growth hormone, interferon and factor VIII, viral antigens, and other animal hormones.

The ribosome binding site is one of the elements involved in such expression. It covers the region about 20 nucleotides on both sides of the initiation codon and contains the Shine-Dalgarno sequence usually 6-10 nucleotides upstream from the initiation codon. The 20 nucleotides after the initiation codon includes the beginning of the gene sequence inserted for expression and often cannot be subjected to modifications without changing the amino acid sequence of the gene. Therefore, in a practical sense, manipulation of the ribosome binding site can only be carried out at the region upstream from the initiation codon. The ribosome binding site is known to function best if it contains certain bases but there is no known requirement for any particular base in a particular sits except that the Shine-Dalgarno sequence is generally purine-rich. The subtle differences among various known ribosome binding site sequences do not provide an obvious comparison to predict which genes will be highly and which will be poorly expressed when associated therewith. A preferred embodiment of the present invention utilizes sequences that are rich in A and T nucleotides to flank the Shine-Dalgarno sequence thereby producing ribosome binding sites that have an increased number of adenine and thymidine residues as compared to the naturally occurring ribosome binding sites from which they are derived.

Naturally occurring BSt is a mixture of heterogeneous proteins, the amino acid sequences of which are known (Paladini, A. C., et al., Molecular Biology of Growth Hormone, CRC Reviews in Biochem., 15(1):25-56 (1983). The naturally occurring mixtures have been purified from pituitary glands of cattle. The commercial potential for using BSt for promoting growth and lactation is well recognized and documented by biological studies on both dairy and feed cattle (Eppard, P. J. and Bauman, D. E., The Effect of Long-Term Administration of Growth Hormone on Performance of Lactating Dairy Cows; and Bausan, D. E., Effect of Growth Hormone on Growth Rates and Mammary Development of Ruminants, Proc. 1984 Cornell Nutrition Conference for Feed Manufacturers, pp. 5-17, published by Cornell University, Ithaca, N.Y.).

Recombinant bovine somatotropin (rBSt) can be produced in transformed microorganisms using a variety of recombinant genetic plasmids (see, e.g., Seeburg, P. H., et al., "Efficient Bacterial Expression of Bovine and Porcine Growth Hormones," DNA, 2:37-45 (1983)); European Patent Application 47 600; United Kingdom Patent Application, GB 2073245A; Schoner, B. E., et al., Role of mRNA Translational Efficiency in Bovine Growth Hormone Expression in *Escherichia coli*, PNAS USA, 81:5403-5407 (1984); European Patent Application 103 395; and European Patent Application 111,814). These documents relate to the insertion or deletion of bases at the 5' end of the BSt gene creating a protein different from the naturally-occurring polypeptide or, to changes in the BSt CDNA to maximize preferred codons and to reduce secondary structure in the mRNA, or to the use of a runaway plasmid to enhance expression. On the other hand, the instant invention teaches the use of an A T-rich ribosome binding site to produce heterologous polypeptides, and in particular, BSt at a high level.

Methods of culturing and fermenting transformed microorganisms expressing BSt are also referred to in the above-cited documents.

Purification of biologically active rBSt from transformed cells has also been described previously (see, e.g., U.S. Pat. Nos. 4,511,502, 4,511,503, 4,512,922 and 4,518,526; European Patent Application 131 843; and, Schoner, R. G., et al., "Isolation and Purification of Protein Granules from *E. coli* Cells Overproducing BSt," Bio-Tech., 3:151-154 (1985)).

SUMMARY OF THE INVENTION

The instant invention relates to ribosome binding sites enriched in adenine and thymine.

More specifically, the instant invention provides recombinant DNA molecules comprising a sequence of deoxyribonucleotides encoding a heterologous polypeptide and a ribosome binding site operatively linked thereto, wherein the ribosome binding site has an increased number of adenine (A) and thymidine (T) residues as compared to the naturally occurring ribosome binding site from which it is derived or to which it is related.

More specifically the heterologous polypeptide is a somatotropin, preferably porcine, ovine and bovine, and most preferably, bovine somatotropin.

More specifically, the recombinant DNA molecule ribosome binding site deoxyribonucleotide sequence is AAGTTCACGTTATTAAAAATTAAAGAGG-TATATATTAATG or AAGTTCACGTTAT-TAAAAATTAAGGAGGTATATCCATAATG, and preferably for bovine somatotropin, AAGTT-CACGTTATTAAAAATTAAAGAGGTATATAT-TAATGGCCTTCCCAGCT or AAGTTCACGT-TATTAAAAATTAAGGAGGTATATC-GATAATGGCCTTCCCAGCT.

The instant invention also provides DNA molecules comprising a sequence of deoxyribonucleotides selected from AAGTTCACGTTATTAAAAAT-TAAAGAGGTATATATTAATGGCCTTC-CCAGCT, AAGTTCACGTTATTAAAAAT-TAAGGAGGTATATCGATAATGGCCTTC-CCAGCT, AAGTTCACGTTATTAAAAAT-TAAAGAGGTATATATTAATC and AAGTT-CACGTTATTAAAAATTAAGGAGGTATATC-GATAATG.

The instant invention also provides a ribosome binding site having an increased number of A and T residues as compared to the naturally occurring ribosome binding site from which it is derived or to which it is related.

DETAILED DESCRIPTION OF THE INVENTION

Generally, the definitions of nomenclature and descriptions of general laboratory procedures used in this invention can be found in Maniatis, T. et al., *Molecular Cloning, A Laboratory Manual,* Cold Spring Harbor Laboratory, Cold Spring Harbor, N.Y., 1982. The manual is hereinafter referred to as "Maniatis" and is incorporated herein by reference.

All *E. coli* strains are grown on Luria broth (LB), LB with 0.2% glucose, Difco's Antibiotic Medium #2, or M9 medium supplemented with 0.2% glucose and 0.05–0.1% acid-hydrolyzed casein amino acids. Strains resistant to antibiotics are maintained at the drug concentrations described in Maniatis. Transformations are performed according to the method described by Morrison, D. A. (1977), J. of Bact., 132:349–351.

All restriction endonuclease and other DNA modifying enzymes are commercially available and are used according to the manufacturer's instructions.

Restriction fragments are separated by either agarose or polyacrylamide gel electrophoresis and isolated by electroelution (Maniatis).

Large scale and rapid plasmid isolations are done as described in Maniatis.

Protein concentration is determined using the BioRad protein assay kit, based on Coomassie Blue staining.

SDS polyacrylamide gel electrophoresis for protein analysis is performed as described in Morse, L., et al., 1978, J. Virol., 26:389–410.

Western immunoblotting analysis is performed as described in Towbin, H., et al., 1979, Proc. Natl. Acad. Sci., USA, 76:4350–4354.

Colony hybridization is carried out as generally described in Grunstein, M. et al., Proc. Natl Acad. Sci., 72:3961–5 (1975).

Hybridization conditions for oligonucleotide probes are as previously described by Goeddel, D. V. et al., Nature, 290:20–26 (1981).

For restriction endonuclease digestion to analyze transformants, mini-lysates of plasmid DNA are prepared according to the method of Holmes, D. S. et al., Analyt. Biochem., 114:193 (1981), or the alkaline lysis procedure described in Kaniatis. Large scale plasmid preparation is by CsCl sedimentation, according to procedures described in Maniatis.

Plasmid sequencing is done according to the dideoxy chain termination method of Wallace, R. B. et al., Gene, 16:21–26 (1981), or the chemical degradation method of Mmam, A. M. and Gilbert, W., Methods in Enzymology, 65:499–560 (1980).

Oligonucleotides are chemically synthesized according to the solid phase phosphoramidite triester method (Beaucage, S. L. and Caruthers, M. H., Tetrahedron Latts., 22(20):1859–1862 (1981)) using an automated synthesizer, as described in Needhan-VanDevanter, D. R. et al., Nucleic Acids Res., 12:6159–6168 (1984). Oligonucleotides are purified by preparative gel electrophoresis using 12–20% polyacrylamide with 7M urea. The appropriate band is eluted from the gel by incubating the gel slice in 0.54M ammonium acetate at 37°. The salt is removed by absorption of the oligonucleotides on a Waters Sep-Pak C18 column and eluting with acetonitrile:$H_2O$ (40:60 V:V).

For high level expression of a desired cloned gene in a prokaryotic system, it is essential to construct expression vectors that contain, at a minimum, a strong promoter to direct mRNA transcription, a ribosome binding site for translational initiation, and, usually, a transcription terminator (collectively, "the expression control sequences") all of which are operatively linked to the desired gene. The term "operatively linked" includes having an appropriate start signal in front of the gene encoding the desired product and maintaining the correct reading frame to permit expression of the inserted gene under the control of the expression control sequences and synthesis of the desired product encoded for by that gene. Since the accumulation of large amounts of a gene product often inhibits cell growth and sometimes causes cell death, the promoter chosen to direct the synthesis of the product should be regulated in such a way that cell growth can reach high densities before the promoter is induced. Examples of regulatory regions suitable for this purpose are the promoter and operator region of the *E. coli* tryptophan biosynthetic pathway (trp promoter) and the leftward promoter of phage lambda ($P_L$). The trap promoter is repressed in the presence of tryptophan and can be induced by tryptophan starvation or by the addition of the inducer endole acrylic acid (Yanofsky, C., et al., J. Bacteriol., 158:1018–1024 (1984)). Promoter $P_L$ is controlled by the repressor cI. With a temperature-sensitive mutation in the cI gene, e.g., cI857, $P_L$ can be induced at temperatures above 38° C. (Herskowitz, I. and Hagen, D. , 1980, Ann. Rev. Genet., 14:399–445). Most preferred are expression vectors having restriction enzyme sites for insertion of genes to be expressed at an appropriate distance from the Shine-Dalgarno sequence.

In *E. coli,* the start codon, usually ATG, should be located in conjunction with an appropriate ribosomal binding site sequence for efficient expression of a gene (Gold, L., et al., 1981, Ann. Rev. Microbiol., 35:365–403; Scherer, G. F. E., et al., 1980, Nucleic Acids Res. 17:3895–3906).

To synthesize intracellularly a protein encoded by a eukaryotic gene from its cDNA sequence in *E. coli* and other prokaryotes, it is expedient to remove the 5' untranslated region and the sequence coding for the signal peptide and to supply an initiation codon for translation initiation of the sequence coding for the mature protein. It may also be necessary to replace some of the coding sequence for the mature protein with chemically synthesized oligonucleotides to maximize translation efficiency. The preferred DNA coding sequence of the present invention is the BSt cDNA sequence modified at the 4th codon by changing GCC to GCT. The preferred vector of this invention comprises a pBR322 replicon which expresses the modified bovine somatotropin at particularly high levels. Vectors other than pBR322-derived plasmids can also be used. pBR322 has a ColE1 replicon. Other useful plasmids with ColE1 replicons include pKC7, pAT153, and pBR325. They differ from pBR322 only in their drug resistance makers. Other useful vectors include pACYC184 (pI5A replicon), pNO1523 (pKB1 replicon), pLG338 (pSC101 replicon), and pBEU50 (R1 replicon) (Maniatis; Pouvels, P. H., et al, *Cloning Vectors*, Elsevier, N.Y. 1985). Also useful are pURA (R1 and ColEl replicon; U.S. application Ser. No. 016,294), pUC19 (Yanisch-Perron, C., et al, Gene, 33:103–119 1985) and pHC314 (Boros, I., et al, Gene 30:257–260 1984).

As noted above, the isolation and purification of mammalian somatotropins from recombinant microorganisms is known (see, e.g., U.S. Pat. Nos. 4,511,502, 4,512,922 and 4,518,526; European Patent Application 131,843; and Schoner, R. G., et al., Isolation and purification of protein granules from *E. coli* cells overproducing BGH, Bio-Technology, 3:151–154). In summary, the process involves lysing the recombinant microorganisms, selective centrifugation, reshuffling of any non-native disulfide bonds to the native configuration and column chromatography.

Conventions used to represent plasmids and fragments in Charts 1–4 are as follows: The single line figures on the charts represent both circular and linear double-stranded DNA with translation initiation or transcription occurring in the direction of the arrow where indicated below a promoter or structural gene. Asterisks (*) represent the bridging of nucleotides to complete the circular form of the plasmids. Fragments do not have asterisk Karks because they are linear pieces of double-stranded DNA. Endonuclease restriction sites are indicated above the line. Genes are indicated below the line. The relative spacings between these components do not indicate actual distances but are only meant to indicate relative positions on the illustrated DNA sequence.

Constructions of plamides pTrp-BSt102 and pTrp-BStm4, containing the native BSt cDNA sequence and a cDNA modified at the fourth alanine codon from GCC to CCT, respectively, are fully described in U.S. patent application Ser. No. 016,294. In summary, the expression vector pTrp1 is derived from pSK4 (Kaytes, P. S. et al., 1986, J. of Biotechnology, 4:205–218). pTrp1 contains the promoter and operator sequence of the tryptophan biosynthetic pathway (trp promoter) of *E. coli*, the Shine-Dalgarno sequence of the trpL gene, the replication origin from pBR322 and a gene for ampicillin resistance. pTrp1 also has a unique ClaI site following the trpL Shine-Dalgarno sequence and a unique KpnI/Asp718 sits immediately after the initiation codon ATG. A gene having an initiation codon which is inserted at the ClaI site of pTrp1 is expressed with no extraneous amino acids.

The 494 bp PvuII fragment containing the cDNA sequence coding for amino acid residues 24 to 188 of BSt is isolated from pLG23 (deposited with the Northern Regional Research Laboratory in Peoria, Ill., USA under Accession Number NRRL B12436) and inserted into the blunt-ended KpnI site of pTrp1 to produce a BSt cDNA sequence lacking the codons for the first 22 amino acid residues. The resulting plasmid is designated pTrp-BStm1. For ease of manipulation of the truncated BSt sequence, the PvuII site at the codon for amino acid residue 188 is removed by replacing the BSt 3' end between the NstII and BamHI sites with the appropriate oligonucleotides. The resulting plasmid is designated pTrp-BSta1b. To provide the missing BSt sequence at the 5'end, the small ClaI to PvuII region is also replaced by the appropriate oligonucleotides. The resulting plasmids, pTrp-BSt102 and pTrp-BSta4, have the BSt sequence downstream from the trp promoter and the trpL ribosome binding site. Plasmid pTrp-BSt102 has no changes in the beginning of the BSt coding sequence while pTrp-BStm4 has the fourth codon for alanine changed from GCC to GCT. These plasmids are shown in Chart 1.

EXAMPLE 1

Construction of a Plasmid for BSt Expression having an A T-Rich Ribosome Binding Site To construct plasmids for expressing BSt with ribosome binding sites having an increased number of A and T residues as compared to the starting ribosome binding sites, 2 oligonucleotides are used to replace the HpaI to ClaI region in pTrp-BStm4.

Referring now to Chart 2, pTrp-BStm4 is treated with HpaI and ClaI. The HpaI cleavage site is located in the trp promoter sequence and the ClaI cleavage site is located immediately upstream from the initiation codon ATG. To remove all the guanine (G) and cytosine (C) nucleotides in the ribosome binding site except in the Shine-Dalgarno sequence, the CG overhang produced by ClaI digestion is removed by mung-bean nuclease. The fragment so produced (fragment 1) is then legated to fragment 2 (Chart 2) which comprises 2 complementary oligonucleotides chemically synthesized as set forth above and annealed together. Because fragment 2 can legate to fragment 1 in two orientations, the desired orientation in relation to the Shine-Dalgarno sequence (GAGG) which is closer to the initiation codon ATG, is identified by sequencing. The resulting plasmid is designated pAT-BStm4. In a similar manner pTrp-BSt102 is treated with HpaI, ClaI and mung-bean nuclease and legated to fragment 2 to generate pAT-102.

The starting and resulting sequences between the +1 base of the mRNA and the fourth codon of BSt in pTrp-BSt102, pAT-BSt102, pTrp-BStm4 and pAT-BStm4 are shown in Chart 3.

EXAMPLE 2

BSt Expression Using a Plasmid having an A T-Rich Ribosome Binding Site

To test for BSt expression using the expression plasmids of Example 1, the plasmids were transformed into competent *E. coli* strains, K12 (ATCC #e23716) and D112 (U.S. patent application Ser. No. 016,294). The cultures were grown overnight in LB media containing 0.2% glucose, 100 μg/ml ampicillin and 100 μg/ml tryptophan. The overnight cultures were diluted 50- to 100-fold in M9 medium containing 0.2% glucose, 0.05% acid-hydrolyzed autoclaved casein amino acids and 100 μg/ml ampicillin and grown at 30° or 37° with aeration until the OD at 550 nm was 0.3 to 0.4.

Samples were taken from the induction cultures and analyzed by SDS-polyacrylamide gel electrophoresis. The gels were stained with Coomassie Blue and were scanned to determine the amount of visible BSt. The gels were also used for Western imunoblotting analysis. The results are set forth in Table 1. The values for low level expression are from immunoblotting analysis and the values for high level expression are from SDS-PAGE.

Porcine and ovine somatotropins can be made in a similar fashion.

EXAMPLE 3

Construction of a Second Plasmid for BSt Expression having an A T-Rich Ribosome Binding Site Plasmid pTrp2-BStm4 is constructed similarly to pAT-BStm4 (Example 1) except that the two complementary oligonucleotides used have the sticky end of ClaI and therefore they are cloned into pTrp-BStm4 treated with HpaI and ClaI. The difference between pTrp2-BStm4 and pAT-BStm4 is that the ribosome binding site in pTrp2-BStm4 is less A-T rich than in the ribosome binding site in pAT-BStm4 (see Chart 5).

EXAMPLE 4

BSt Expression Using a Second Plasmid having an A T-Rich Ribosome Binding Site

Plasmid pTrp2-BStm4 was transformed into E. coli strains K12 and D112, induced and analyzed for expression essentially as set forth in Example 2. The results are shown in Table 1.

TABLE 1

| Plasmid | BSt Expression % of Total Protein | |
| --- | --- | --- |
| | K12 | D112 |
| pTrp-BSt102, trpL ribosome binding site, no changes at beginning of BSt | <0.01 | <0.01 |
| pAT-BSt102, AT-rich ribosome binding site, no changes at beginning of BSt | <0.01 | 1 |
| pTrp-BStm4, trpL ribosome binding site ala 4 changed from GCC to GCT | <1 | 1 |
| pAT-BStm4, AT-rich ribosome binding site ala 4 changed from GCC to GCT | >10 | >20 |
| pTrp2-BStm4, AT-rich ribosome binding site ala 4 changed from GCC to GCT | 2 | 5 |

The results in Table 1 demonstrate that the very low level expression of the BSt cDNA sequences can be increased by the AT-rich ribosome binding sites, especially in the D112 host. The low level expression of the cDNA sequence modified at the ala 4 codon can be enhanced to greater than 20% of total cellular protein by the A T-rich ribosome binding site.

EXAMPLE 5

Enhanced Expression of Human Tumor Necrosis Factor α (TNF α) with an A T-Rich Ribosome Binding Site A) Construction of an Expression Vector Containing an A T-Rich Ribosome Binding Site To insert cloned genes behind an A T-rich ribosome binding site, the expression vector pTrp2 is constructed. The ribosome binding site area in pTrp-conSD (K. A. Curry and C-S. C. Tomich, "Effect of Ribosoue Binding Site on Gene Expression in E. coli", DNA, in press (1988)) is replaced with oligonucleotides containing an A T-rich sequence. As shown in Chart 3, the ribosome binding site region in pTrp-conSD is removed by treatment with HpaI and ClaI. The resulting fragment 3 is ligated to two complementary oligonucleotides with HapI and ClaI ends to yield pTrp2. Both pTrp-conSD and pTrp2 contain the promoter and operator sequence of the tryptophan biosynthetic pathway (trp promoter) of E. coli, a ribosome binding site sequence with GGACG as the Shine-Dalgarno sequence, a unique ClaI site following the Shine-Dalgarno sequence, the replication origin from pBR322 and a gene for ampicillin resistance. The ribosome binding site sequence is AAGTTCACGTAAGGAGGATATCGATAATG in pTrp-conSD and AAGTTCACGTTAT- TAAAAATTAAGGAGGTATATCGATAATG in pTrp2. The difference between these two sequences is that the ribosome binding site in pTrp2 is more A T-rich than in pTrp-conSD from which it is derived.

B) Construction of Plasmids for Expression of TNF α

The gene coding for TNF α is purchased from British Bio-technology Limited (Brook House, Watlington Road, Cowley, Oxford, OX45LY, UK). This gene has several unique restriction endonuclease sites. A 590 bp SnaBI-BamHI fragment can be isolated from this gene which contains the mature TNF α sequence truncated for the first two codons. This fragment, together with two complementary oligonucleotides to supply the first two codons, is cloned into the expression vectors pTrp-conSD and pTrp2. As shown in Chart 4, pTrp-conSD and pTrp2 are treated with Cl&I and BamHI to yield fragments 5 and 6, respectively. Fragment 5 is legated to fragments 7 (SnaBI-BamHI fragment containing the truncated TNF α gene) and 8 (oligonucleotides supplying the beginning of TNF α sequence and with ClaI and SnaBI ends) to yield pTrp-conSD-TNFα. Similarly, fragment 6 is ligated with fragments 7 and 8 to yield pTrp2-TNFα.

C) Expression of TNF α

Plasmids pTrp-conSD-TNFα and pTrp2-TNFα are transformed into E. coli strain JM103, induced for expression, and analyzed for expression essentially as set forth in Example 2. The level of TNF α expression from pTrp-conSD-TNFα and pTrp2-TNFα are about 5% and 30% of the total cell protein, respectively. Therefore, the A T-rich ribosome binding site increases TNF α expression.

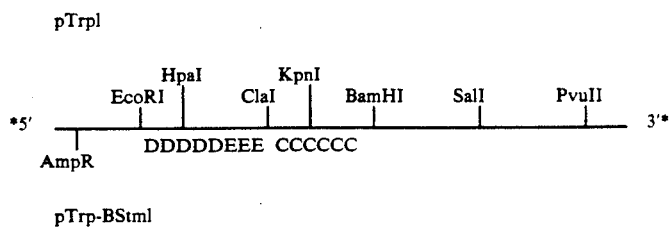

Chart 1. List of plasmids

Chart 1. List of plasmids

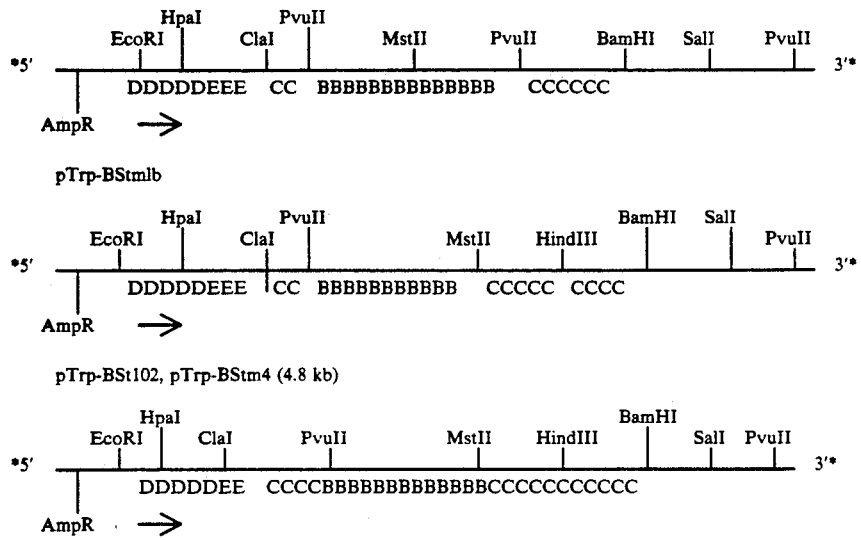

AmpR = Ampicillin resistance
D = Trp promoter/operator
E = Ribosome binding site
C = Synthetic sequence
B = BSt sequence

Chart 2. Construction of pAT-BStm4 a) pTrp-BStm4 is treated with HpaI, ClaI and Mung-bean nuclease to obtain fragment 1.

Fragment 1

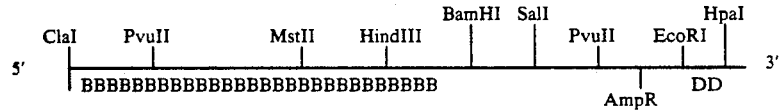

b) Two oligonucleotides are annealed to yield fragment 2.

Fragment 2

```
                    1
5' AACTAGTACGCAAGTTCACGTTATTAAAAATTAAAGAGGTATATAT
   TTGATCATGCGTTCAAGTGCAATAATTTTTAATTTCTCCATATATA
                                                  2
``` c) fragments 1 and 2 are ligated to yield pAT-BStm4 (4.8 Kb)

pAT-BStm4

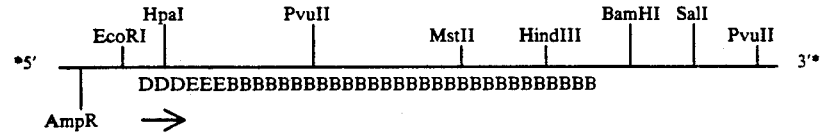

AmpR = Ampicillin resistance
D = Trp promoter/operator
E = Ribosome binding site
C = Synthetic sequence
B = BSt sequence

Chart 3. Construction of pTrp2 a) pTrp-conSD is treated with HpaI and ClaI to obtain fragment 3 (4.6 kb).

Fragment 3

Chart 3. Construction of pTrp2

```
     ClaI KpnI HindIII BamHI SalI PvuII  EcoRI  HpaI
5'   |----|----|-------|-----|----|------|------|   3'
                                         |  DDD
                                        AmpR
``` b) Two complementary oligonucleotides are annealed (fragment 4) and ligated to fragment 3 to yield pTrp2 (4.6 kb).

Fragment 4

AACTAGTACGCAAGTTCACGTTATTAAAAATTAAGGAGGTATAT
TTGATCATGCGTTCAAGTGCAATAATTTTTAATTCCTCCATATAGC pTrp2 (4.6 kb)

```
           EcoRI      ClaI KpnI HindIII BamHI SalI PvuII
*5'  _____|_____|____|____|_____|_____|____|_____ 3'*
      |     DDDDEEE
     AmpR
```

AmpR = Ampicillin resistance
D = Trp promoter/operator
E = Shine Dalgarno sequence

Chart 4. Construction of pTrp-conSD-TNFα and pTrp2-TNFα a) pTrp-conSD is treated with ClaI and BamHI to yield fragment 5. pTrp2 is treated with ClaI and BamHI to yield fragment 6.

Fragments 5 and 6 (4.6 kb)

```
     BamHI SalI PvuII       EcoRI         ClaI
5'   |-----|----|-----------|-------------|   3'
                       |         DDDDEEE
                      AmpR
``` b) The TNF α gene is treated with SnaBI and BamHI to isolate fragment 7 (460 bp).

Fragment 7

```
     SnaBI              SalI                        BamHI
5'   |------------------|---------------------------|   3'
     TTTTTTTTTTTTTTTTTTTTTTTTTTTTTTTTTTTTTTTTTTT
``` c) Two complementary oligonucleotides are annealed to yield fragment 8.

Fragment 8

CGATAATGGTAC
TATTACCATG d) Fragments 5, 7 and 8 are ligated to yield pTrp-conSD-TNFα and fragments 6, 7 and 8 are ligated to yield pTrp2-TNFα.

pTrp-conSD-TNFα and pTrp2-TNFα (5.1 kb)

```
                                              BamHI  PvuII
         EcoRI     ClaI    SnaBI     SalI     SalI
*5' _____|_____|_____|_____|_____|___|____ 3'*
      |     DDDDEEE TTTTTTTTTTTTTTTTTTTTT
     AmpR
```

AmpR = Ampicillin resistance
D = Trp promoter/operator
E = Shine Dalgarno sequence
C = Synthetic sequence
T = TNF α sequence

Chart 5. Ribosome Binding Site Sequences in Plasmids for BSt Expression* pTrp-BSt102

AAGTTCACGTAAAAAGGGTATCGATAATG | GCCTTCCCAGCC pAT-BSt102

AAGTTCACGTTATTAAAAATTAAAGAGGTATATATTAATG | GCCTTCCCAGCC pTrp-BStm4

AAGTTCACGTAAAAAGGGTATCGATAATG | GCCTTCCCAGCT pAT-BStm4

AAGTTCACGTTATTAAAAATTAAAGAGGTATATATTAATG | GCCTTCCCAGCT pTrp2-BStm4

AAGTTCACGTTATTAAAAATTAAGGAGGTATATCGATAATG | GCCTTCCCAGCT

*The ribosome binding sites useful for expressing heterologous polypeptides are indicated to the left of the vertical lines. The sequences to the right of the vertical lines comprise part of the BSt genes.

We claim:

1. A recombinant DNA molecule consisting essentially of:

AAGTTCACGTTATTAAAAATTAAAGAGG-TATATATTAATG or

AAGTTCACGTTATTAAAAATTAAGGAGG-TATATCGATAATGGCCTTCCCAGCT.

2. A recombinant DNA molecule according to claim 1 consisting essentially of:

AAGTTCACGTTATTAAAAATTAAAGAGG-TATATATTAATGGCCTTCCCAGCT or

AAGTTCACGTTATTAAAAATTAAGGAGG-TATATCGATAATGGCCTTCCCAGCT.

3. A recombinant DNA vector containing the DNA molecule of claim 2, selected from the group consisting of pAT-BStm4 and pTrp2-BStm4.

4. A recombinant DNA molecule according to claim 1, additionally comprising an operatively linked sequence of deoxyribonucleotides that encode a heterologous polypeptide.

5. A recombinant DNA molecule according to claim 4, wherein the heterologous polypeptide is a somatotropin.

6. A recombinant DNA molecule according to claim 5, wherein the somatotropin is selected from porcine, ovine and bovine somatotropin.

7. A recombinant DNA molecule according to claim 6, wherein the somatotropin is bovine somatotropin.

* * * * *